United States Patent [19]

Briner

[11] Patent Number: 5,200,535
[45] Date of Patent: Apr. 6, 1993

[54] CYCLOHEXANONE DERIVATIVES

[75] Inventor: Paul H. Briner, Canterbury, England

[73] Assignee: Shell Research Limited, United Kingdom

[21] Appl. No.: 746,977

[22] Filed: Aug. 19, 1991

[30] Foreign Application Priority Data

Sep. 3, 1990 [GB] United Kingdom ............... 9019192
Sep. 3, 1990 [GB] United Kingdom ............... 9019193
Sep. 3, 1990 [GB] United Kingdom ............... 9019194

[51] Int. Cl.⁵ ............... C07D 303/12; C07D 301/12; C07C 49/543; C07C 49/603
[52] U.S. Cl. .................... 549/546; 558/414; 560/53; 562/452; 562/463; 564/169; 564/443; 568/31; 568/37; 568/43; 568/329; 568/705
[58] Field of Search ............ 568/329, 31, 37, 43, 568/705; 549/546; 558/414; 560/53; 562/452, 467; 564/169, 443

[56] References Cited

FOREIGN PATENT DOCUMENTS 0267778 5/1988 European Pat. Off.
2180236 3/1987 United Kingdom.

OTHER PUBLICATIONS

Kozikowski et al "J. Org. Chem." (1986) 51 pp. 3400-3402.
Berk et al, "J. Org. Chem." (1988) 53 pp. 5789-5791.
O'Connor et al, "Tetrahdron Letters" vol. 29, No. 32 pp. 3903-3906 (1988).
Shapiro et al "J. Org. Chem.", vol. 41, No. 9, 1976.

Primary Examiner—Joseph E. Evans

[57] ABSTRACT

The invention provides cyclohexanone derivatives of the general formula

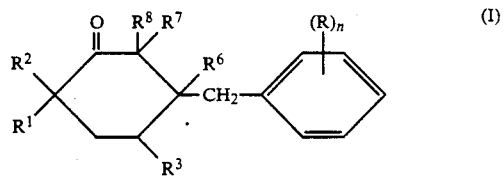

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$, $R^2$ and $R^3$ independently represent a hydrogen atom or an alkyl group; $R^6$ and $R^7$ together represent a single carbon-carbon bond or an epoxy group; and $R^8$ represents a hydrogen atom or a hydroxyl group; with the proviso that when $R^6$ and $R^7$ together represent an epoxy group then $R^8$ represents a hydrogen atom; and a process for their preparation. Compounds of formula I are useful as intermediates in the preparation of certain fungicidally active cyclopentane derivatives.

5 Claims, No Drawings

CYCLOHEXANONE DERIVATIVES

This invention relates to certain cyclohexanone derivatives, which are useful as intermediates in the preparation of fungicidally active cyclopentane derivatives, and a process for their preparation.

According to the present invention there is provided a compound of the general formula

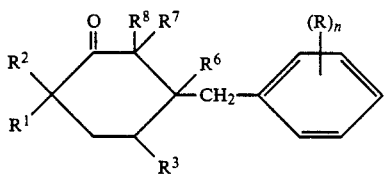

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$, $R^2$ and $R^3$ independently represent a hydrogen atom or an alkyl group; $R^6$ and $R^7$ together represent a single carbon-carbon bond or an epoxy group; and $R^8$ represents a hydrogen atom or a hydroxyl group; with the proviso that when $R^6$ and $R^7$ together represent an epoxy group then $R^8$ represents a hydrogen atom.

When any of the foregoing substituents represents or contains an alkyl substituent group, this may be linear or branched and may contain up to 12, preferably up to 6, and especially up to 4 carbon atoms. A cycloalkyl substituent group may contain 3 to 8, preferably 3 to 6, carbon atoms.

It is preferred that $R^1$, $R^2$ and $R^3$ independently represent a hydrogen atom or a $C_{1-4}$ alkyl, particularly a methyl, group.

Preferably, R represents a halogen, especially a chlorine atom.

A particularly preferred sub-group of compounds of formula I is that in which n is 1, R represents a chlorine atom, preferably substituted at the 4-position of the phenyl ring, $R^1$ and $R^2$ both represent a hydrogen atom or both represent a methyl group and $R^3$ represents a hydrogen atom or methyl group.

The present invention also provides a process for the preparation of a compound of formula I as defined above which comprises (a) reacting a compound of the general formula

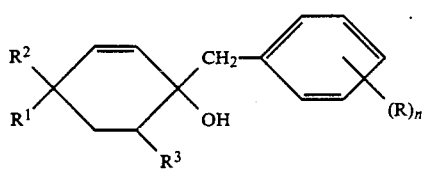

in which n, R, $R^1$, $R^2$ and $R^3$ are as defined above, with an oxidising agent to produce a compound of formula I in which $R^6$ and $R^7$ together represent a single carbon-carbon bond and $R^8$ represents a hydrogen atom;

(b) if desired, reacting the compound of formula I formed in (a) with hydrogen peroxide in the presence of a base to produce a compound of formula I in which $R^6$ and $R^7$ together represent a epoxy group and $R^8$ represents a hydrogen atom; and (c) if desired, reacting the compound of formula I formed in (b) with a compound of the general formula $$MOR^5 \qquad (III)$$

in which $R^5$ represents a hydrogen atom or an alkyl, preferably a $C_{1-6}$ tertiary alkyl and especially a $C_{4-6}$ tertiary alkyl, or cycloalkyl, preferably a $C_{3-6}$ cycloalkyl, group and M represents an alkali metal, preferably a sodium or potassium, atom in the presence of a polar solvent to produce a compound of formula I in which $R^6$ and $R^7$ together represent a single carbon-carbon bond and $R^8$ represents a hydroxyl group.

Preferably, the oxidising agent in step (a) is a chromium (VI) salt such as an alkali metal dichromate, particularly sodium dichromate or potassium dichromate. When an alkali metal dichromate is used as oxidising agent, the reaction is preferably performed in the presence of an acid. It is also preferred that the acid is a dilute mineral acid, dilute sulphuric acid being especially preferred.

Step (a) may be conveniently carried out in the presence of a solvent. Suitable solvents include ethers, such as diethyl ether. Alternatively, the acid may serve as solvent. The reaction is suitably carried out at a temperature in the range from 0° C. to 70° C., preferably 10° C. to 60° C.

Preferably, the base in step (b) is an inorganic base such as sodium hydroxide, potassium hydroxide or a quaternary ammonium hydroxide.

Step (b) may be conveniently carried out in the presence of a solvent. Suitable solvents include alcohols, such as methanol, ethanol and, especially, tert-butanol. The reaction is suitably carried out at a temperature in the range from −10° C. to 60° C., preferably 0° C. to 50° C.

It is preferred that the polar solvent in step (c) is an alcohol, preferably a $C_{1-6}$ and especially a $C_{4-6}$ tertiary alcohol. If an alcohol is used as solvent, it is preferred that the alkyl moiety in the alcohol is the same as $R^5$ in the compound of formula III. For instance, if the compound of formula III is potassium tert-butoxide, it is preferred that the alcohol is tert-butanol. The reaction is conveniently carried out at a temperature from 30° C. to the reflux temperature of the solvent.

Compounds of formula II may be conveniently prepared by reacting a compound of formula

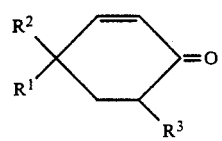

in which $R^1$, $R^2$ and $R^3$ are as defined above, with a compound of the general formula

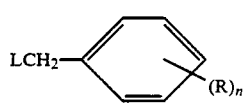

in which R and n are as defined above and L represents an organometallic group, such as lithium or the group —MgHal where Hal represents a chlorine or bromine atom. The compounds of formula II and a process for their preparation form the subject of copending patent application T 689.

Compounds of formula III, IV and V are known compounds or can be prepared by processes analogous to known processes.

The compounds of formula I are useful as intermediates in the preparation of fungicidally active cyclopentane derivatives of the general formula

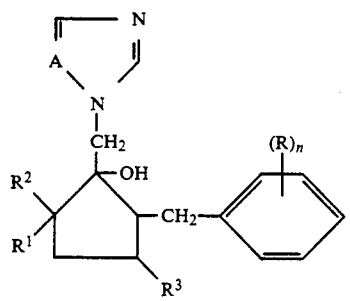

(VI)

in which n, R, $R^1$, $R^2$ and $R^3$ are as defined above and A represents a nitrogen atom or a CH group. Certain compounds of formula VI are the subject of co-pending patent applications GB-A1-2180236 and EP-A2-0267778. The compounds disclosed in EP-A2-0267778 and GB-A1-2180236 exist in two stereoisomeric forms which have the following structures:

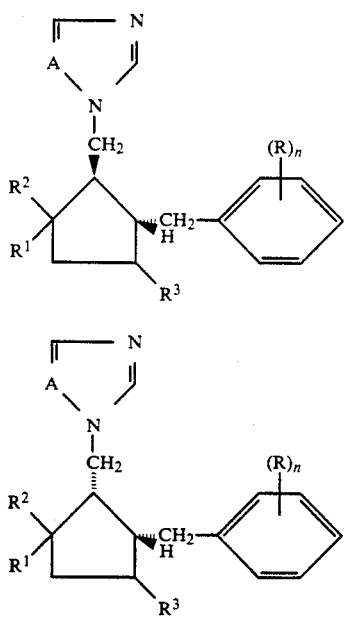

(VIA)

(VIB)

The letters A and B will be used hereinafter to denote compounds having the same stereochemical configuration as isomers A and B above.

Isomers A and B can be separated by, for instance, chromatography and exhibit different fungicidal activity. Generally, isomers of formula VIA exhibit greater fungicidal activity than isomers of formula VIB. The process used to synthesise compounds of formula VIA from compounds of formula I in which $R^6$ and $R^7$ together represent a single carbon-carbon bond and $R^8$ represents a hydroxyl group is set out in the following reaction scheme:

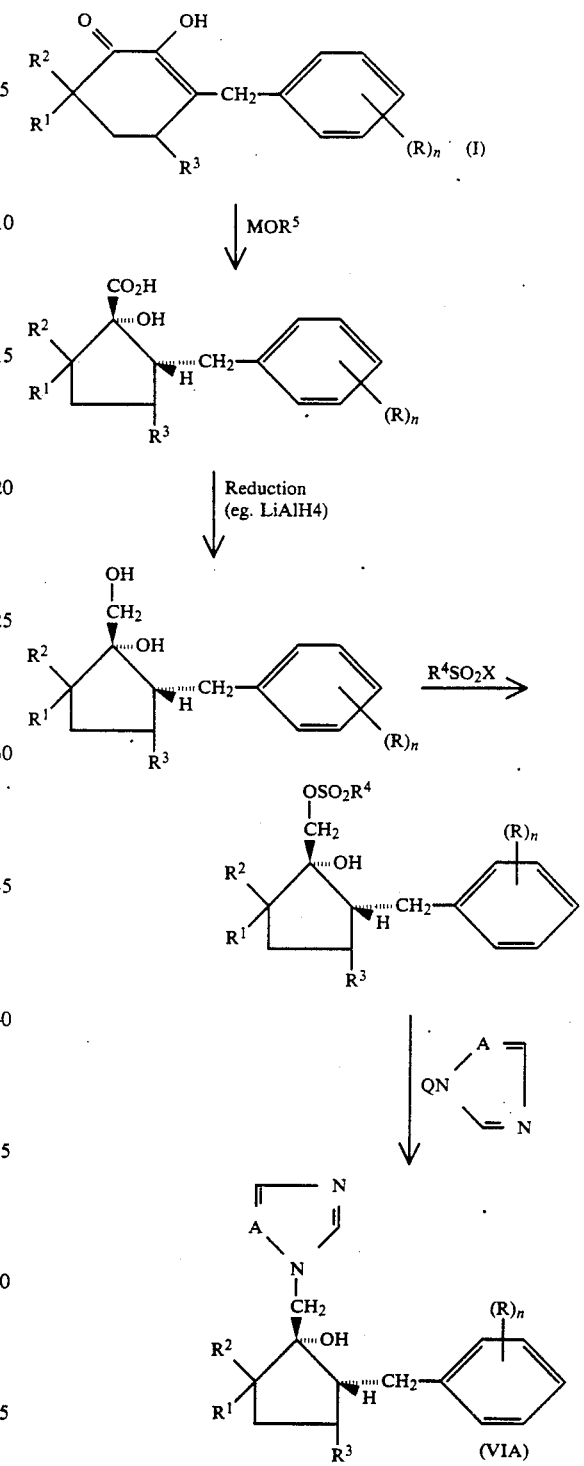

In the above reaction scheme, n, R, $R^1$, $R^2$, $R^3$, $R^5$, M and A are as previously defined, $R^4$ represents an optionally substituted alkyl or aryl group, preferably a $C_{1-4}$alkyl or a phenyl group each optionally substituted by one or more substituents selected from halogen atoms, nitro, cyano, hydroxyl, $C_{1-4}$alkyl, $C_{1-4}$haloalkyl, $C_{1-4}$alkoxy, $C_{1-4}$haloalkoxy, amino, $C_{1-4}$alkylamino, di-$C_{1-4}$alkylamino, $C_{1-4}$alkoxycarbonyl, carboxyl, $C_{1-4}$alkanoyl, $C_{1-4}$alkylthio, $C_{1-4}$alkylsulphinyl, $C_{1-4}$alkylsulphonyl, carbamoyl, $C_{1-4}$alkylamido, $C_{3-8}$cycloalkyl and phenyl groups, X represents a halogen, preferably a chlorine or bromine, atom and Q represents a hydrogen or alkali metal, preferably sodium or potassium, atom. The intermediate compounds and process steps in the above reaction scheme are the subject of copending patent application T 693, copending European patent application no. 89202159.3 and copending British patent application no. 8820607.3.

The invention is further illustrated by the following Examples.

EXAMPLE 1

Preparation of 1-(4-chlorobenzyl)-4,4-dimethylcyclohex-1-en-3-one (n=1, R=4-Cl, $R^1=R^2=CH_3$, $R^3=H$, $R^6$ and $R^7$=single C-C bond, $R^8=H$)

(a) Preparation of 1-(4-chlorobenzyl)-4,4-dimethylcyclohex-2-en-1-ol

A solution of 4-chlorobenzyl chloride (266 g, 1.65 mol) in diethyl ether (200 ml) was added slowly to a stirred mixture of magnesium (42 g, 1.73 mol) in diethyl ether (700 ml) to maintain the mixture at reflux. The mixture was warmed for a further 20 minutes after addition was complete. A solution of 4,4-dimethylcyclohex-2-en-1-one (226 g, 1.82 mol) in diethyl ether (60 ml) was then added dropwise over a period of 30 minutes so as to maintain the mixture at reflux and the mixture stirred overnight. The mixture was then quenched with water (250 ml) and hydrochloric acid (5M, 500 ml), extracted with diethyl ether (3×400 ml), backwashed once with sodium bicarbonate solution (5%w/v) and once with water and then dried with anhydrous magnesium sulphate. The solvent was then flashed off to give 369 g 1-(4-chlorobenzyl) -4,4-dimethylcyclohex-2-en-1-ol as an oil. NMR (in $CDCl_3$ solvent, tetramethylsilane as reference) Characteristic peaks at:

$\delta$(ppm): 0.90, 0.99 (3H, singlet), 2.78 (2H, singlet), 5.40 (1H, doublet, J=11 Hz), 5.50 (1H, doublet, J=11 Hz), 7.17 (2H, doublet, J=8 Hz), 7.26 (2H, doublet, J=8 Hz).

(b) Preparation of 1-(4-chlorobenzyl)-4,4-dimethylcyclohex-1-en-3-one

A solution of the 1-(4-chlorobenzyl)-4,4-dimethylcyclohex-2-en-1-ol (368 g, 1.47 mol) obtained in (a) in 40/60 petroleum (40 ml) was added in a steady stream to a solution of sodium dichromate (217 g, 0.74 mol) in dilute sulphuric acid (250 g, 2.6 mol 98% sulphuric acid in 1.5 liters of water). The reaction mixture was then held at a temperature between 10° and 30° C. and stirred for 40 minutes. Water (500 ml) and diethyl ether (700 ml) were added and the aqueous layer extracted twice with diethyl ether (2×700 ml). The organic phases were then combined and backwashed with saturated sodium bicarbonate solution (1×500 ml) and water (1×500 ml). The solvent was then flashed off to give 349 g crude 1-(4-chlorobenzyl)-4,4-dimethylcyclohex -1-en-3-one as a beige coloured granular solid. Trituration in petrol gave a pure sample of the desired product, m.pt. 87°-90° C.

EXAMPLE 2

Preparation of 1-(4-chlorobenzvl)-1,2-epoxv-4,4-dimethylcyclohexan-3-one (n=1, R=4—Cl, $R^1=R^2=CH_3$, $R^3=H$, $R^6$ and $R^7=$—O—, $R^8=H$)

1726 g (6.945 mol) crude 1-(4-chlorobenzyl)-4,4-dimethylcyclohex-1-en-3-one obtained as described in Example 1 above and ethanol (8630 ml) were charged into a 20 liter reactor and warmed to 40° C. to give a clear pale orange solution. The reaction mixture was then cooled to 18° C and 20% (w/v) sodium hydroxide (650 ml) was added slowly with cooling (ice/water) to maintain this temperature. Keeping the reaction mixture at a temperature between 11° and 20° C., 30% (w/v) aqueous hydrogen peroxide (794 ml, 7 mol) was added over a period of 1 hour and the mixture was then stirred overnight. Water (16 liters) was then added with ice cooling and the reaction mixture stirred for 15 minutes. Centrifugation followed by washing with water (4×2½ liters) yielded an off-white solid which was then air dried to give 1634 g 1-(4-chlorobenzyl)-1,2-epoxy-4,4-dimethylcyclohexan -3-one, m.pt. 69°-70° C.

EXAMPLE 3

Preparation of 1-(4-chlorobenzyl)-2-hydroxy-4,4-dimethylcvclohex-1-en-3-one (n=1, R=4—Cl, $R^1=R^2$—$CH_3$, $R^3=H$, $R^6$ and $R^7=$single C—C bond, $R^8=OH$)

38.7 g (146 mmol) 1-(4-chlorobenzyl)-1,2-epoxy-4,4-dimethylcyclohexan-3-one obtained in Example 2 above was added to a slurry of potassium tert-butoxide (33 g, 294 mmol) in tert-butanol (200 ml) at 40° C. The mixture was then warmed to 60 C and stirred for 2 hours before being cooled in ice and quenched with water (50 ml). 5M Hydrochloric acid (100 ml) was then added slowly followed by water (300 ml). The mixture was then cooled to 0° C., filtered and the residue washed with water (100 ml). Drying under vacuum at 40° C. gave 36.3 g 1-(4-chlorobenzyl)-2-hydroxy-4,4-dimethylcyclohex-1-en-3-one, m.pt. 80–82° C.

EXAMPLE 4

Preparation of 1-(4-chlorobenzyl)-4,4,6-trimethylcyclohex-1-en-3-one (n=1, R=4—Cl, $R^1=R^2=R^3=CH_3$, $R^6$ and $R^7=$single C—C bond, $R^8=H$)

(a) Preparation of 1-(4-chlorobenzyl)-4,4,6-trimethylcyclohex-2-en-1-ol

To a slurry of magnesium turnings (66 g, 2.73 g.a-toms) in diethyl ether (300 ml) was added a solution of 4-chlorobenzyl chloride (418 g, 2.6 moles) in diethyl ether (1500 ml) at such a rate as to maintain gentle reflux. After a further 30 minutes, a solution of 4,4,6-trimethylcyclohex-2-en-1-one (340 g, 2.46 moles) in diethyl ether (350 ml) was added, again maintaining a gentle reflux. After 1 hour the mixture was added into saturated aqueous ammonium chloride (4 liters) and the phases separated. The ether phase was back-washed with water (1 liter) and used directly in the next reaction. A small portion of 1-(4-chlorobenzyl)-4,4,6-trimethylcyclohex-2-en-1-ol was isolated for characterisation (gas chromatography analysis showed two isomers in approximately equal amounts).

NMR (in $CDCl_3$ solvent, tetramethylsilane as reference). Characteristics peak at:

$\delta$(ppm): 0.75, 0.95, 1.00, 1.02, 1.05, 1.07, 1.09 (total 9H), 2.00 (1H,multiplet), 2.57, 2.79 (2H, AB, J=12 Hz), 2.69, 2.94 (2H, AB, J=12 Hz), 4.94 (1H, doublet, J=10 Hz), 5.34 (1H, doublet, J=10 Hz), 7.1–7.4 (4H).

(b) Preparation of 1-(4-chlorobenzvl)-4,4,6-trimethylcyclohex-1-en-3-one

A solution of sodium dichromate (281 g, 0.943 mol) in dilute sulphuric acid (428 g 98% sulphuric acid in 2.5 liters of water) was added to the ethereal solution of 1-(4-chlorobenzyl)-4,4,6-trimethylcyclohex-2-en-1-ol obtained in (a). The reaction mixture was then heated to 50°-60° C. for 3-4 hours, cooled and quenched with water (2 liters) and diethyl ether (1 liter). The phases were separated and the organic phase was washed with 20% (w/v) sodium hydroxide (2×500 ml) to give a clear pale brown solution. Stripping off the solvent gave a mixture of crystalline solid and oily liquid which was then triturated in 60/80 petroleum (1 liter) at 0° C. and filtered to give 315 g 1-(4-chlorobenzyl)-4,4,6-trimethylcyclohex-1-en-3-one as a crystalline white solid, m.pt 76°-77° C.

EXAMPLE 5

Preparation of
1-(chlorobenzyl)-1,2-epoxy-4,4,6-trimethylcyclohexan-3-one (n=1, R=4—Cl, $R^1=R^2=R^3=CH_3$, $R^6$ and $R^7=$—O—, $R^8=H$)

The 1-(chlorobenzyl)-4,4,6-trimethylcyclohexan-3-one (315 g, 1.2 mol) obtained in Example 4 above was added to methanol (1500 ml) and the mixture warmed to 40° C. to give a clear yellow solution. The solution was then cooled to 10° C. and aqueous sodium hydroxide (25 g in 112 ml water) was added over a period of 10 minutes. Whilst maintaining the temperature of the reaction mixture between 15° and 20° C., 30% (w/v) aqueous hydrogen peroxide (138 ml, 1.2 mol) was added over a period of 30 minutes and the mixture was then stirred overnight. A further 30 ml was then added and the mixture stirred for 2¼ hours. The reaction mixture was then concentrated under reduced pressure and diluted with water (2 liters) and diethyl ether (1.5 liters). The aqueous layer was then extracted with diethyl ether (2×0.5 liters), dried and the solvent flashed off to give 1-(4-chlorobenzyl)-1,2-epoxy-4,4,6-trimethylcyclohexan-3-one as a crystalline white solid (271 g), m.pt. 58°-59° C.

EXAMPLE 6

Preparation of 1-(4-chlorobenzyl)-2-hydroxy-4,4,6-trimethylcyclohex-1-en-3-one (n=1, R=4—Cl, $R^1=R^2=R^3=CH_3$, $R^6$ and $R^7=$single C—C bond, $R^8=OH$)

Flake potassium hydroxide (30.4 g, 3 equivalents) was added to a solution of the 1-(4-chlorobenzyl)-1,2-epoxy-4,4,6-trimethylcyclohexan-3-one (43 g, 0.154 mol) obtained in Example 5 above in tert-butanol (200 ml) at 40°-50° C. and the mixture brought to reflux for 3 hours. Gas chromatography showed the presence of the desired 1-(4-chlorobenzyl)-2-hydroxy-4,4,6-trimethylcyclohex-1-en-3-one and a small portion of this was isolated as an oil for characterisation. NMR (in CDCl₃ solvent, tetramethylsilane as reference) Characteristic peaks at:

δ(ppm): 1.04(3H, doublet, J=7 Hz), 1.08, 1.16 (3H, singlet), 1.57(1H, double doublet, J=10, 13 Hz), 1.72(1H, double doublet, J=5, 13 Hz), 2.51(1H, multiplet), 3.41, 3.92(2H, AB, J=15 Hz), 6.31(1H, broad singlet), 7.12, 7.23 (2H, AB, J=9 Hz)

I claim:

1. A compound of the formula

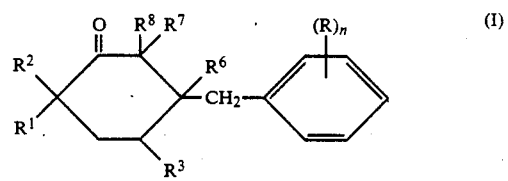

in which n represents an integer from 0 to 5;

each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group;

$R^1$, $R^2$ and $R^3$ independently represent a hydrogen atom or an alkyl group;

$R^6$ and $R^7$ together represent a single carbon-carbon bond and $R^8$ represents a hydroxyl group, or, $R^6$ and $R^7$ together represent an epoxy group and $R^8$ represents a hydrogen atom.

2. A compound according to claim 1 in which $R^1$, $R^2$ and $R^3$ independently represent a hydrogen atom or a $C_{1-4}$ alkly group.

3. A compound according to claim 1 in which $R^1$, $R^2$ and $R^3$ independently represent a hydrogen atom or a methyl group.

4. A compound according to claim 1 in which R represents a halogen atom.

5. A compound according to claim 1 in which n is 1, R represents a chlorine atom, $R^1$ and $R^2$ both represent a hydrogen atom or both represent a methyl group and $R^3$ represents a hydrogen atom or a methyl group.

* * * * *